(12) United States Patent
Takeuchi et al.

(10) Patent No.: US 9,867,919 B2
(45) Date of Patent: Jan. 16, 2018

(54) PRODUCTION METHOD FOR MEDICAL INSTRUMENT AND MEDICAL INSTRUMENT

(71) Applicant: Terumo Kabushiki Kaisha, Shibuya-ku (JP)

(72) Inventors: Kazuhiko Takeuchi, Fujinomiya (JP); Eisuke Sasaki, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 403 days.

(21) Appl. No.: 14/495,179

(22) Filed: Sep. 24, 2014

(65) Prior Publication Data
US 2015/0010433 A1    Jan. 8, 2015

Related U.S. Application Data

(63) Continuation of application No. PCT/JP2013/057291, filed on Mar. 14, 2013.

(30) Foreign Application Priority Data

Mar. 26, 2012   (JP) .................................. 2012-070139

(51) Int. Cl.
*A61M 1/16* (2006.01)
*B01D 63/02* (2006.01)
(Continued)

(52) U.S. Cl.
CPC ......... *A61M 1/1698* (2013.01); *B01D 63/021* (2013.01); *B01D 63/025* (2013.01);
(Continued)

(58) Field of Classification Search
CPC ... A61M 1/1698; B65H 81/02; B01D 63/021; B01D 63/025; B01D 2313/38;
(Continued)

(56) References Cited

U.S. PATENT DOCUMENTS 3,794,468 A    2/1974 Leonard
4,141,836 A *  2/1979 Schael .................. B01D 63/02
                                               210/321.81
(Continued)

FOREIGN PATENT DOCUMENTS

EP    0 562 520 A1    9/1993
GB    2 012 187 A     7/1979
(Continued)

OTHER PUBLICATIONS

Extended European Search Report issued on Oct. 15, 2015, by the European Patent Office in corresponding European Application No. 13770190.0-1356. (7 pages).

(Continued)

*Primary Examiner* — Tatyana Zalukaeva
*Assistant Examiner* — Benjamin Klein
(74) *Attorney, Agent, or Firm* — Buchanan Ingersoll & Rooney PC

(57) ABSTRACT

A production method for a medical instrument includes a plurality of integrated hollow fiber membrane producing a base material forming a cylindrically-shaped body. Each of the hollow fiber membranes sequentially passes through a first point, a second point, a third point, a fourth point, and a fifth point that are set on a core member. In an outward path heading toward the third point from the second point, the hollow fiber membrane reaches the third point from the second point at the shortest distance while being wound in the circumferential direction of the core member. Moreover, in a homeward path heading toward the fifth point from the fourth point, the hollow fiber membrane reaches the fifth point from the fourth point at the shortest distance while being wound in the circumferential direction of the core member in the same direction as in the case of the outward path.

19 Claims, 14 Drawing Sheets

(51) Int. Cl.
*F28D 7/10* (2006.01)
*B65H 81/02* (2006.01)
*F28D 21/00* (2006.01)

(52) U.S. Cl.
CPC ............ *B65H 81/02* (2013.01); *F28D 7/103* (2013.01); *B01D 2313/38* (2013.01); *B01D 2323/42* (2013.01); *F28D 21/0015* (2013.01); *F28D 2021/005* (2013.01)

(58) Field of Classification Search
CPC . B01D 2323/42; F28D 7/103; F28D 21/0015; F28D 2021/005
See application file for complete search history.

(56) References Cited

U.S. PATENT DOCUMENTS

| | | | |
|---|---|---|---|
| 4,336,138 A | | 6/1982 | Taniyama et al. |
| RE31,029 E | | 9/1982 | Schael |
| 4,572,446 A | * | 2/1986 | Leonard ............ B01D 63/021 210/321.79 |
| 5,261,981 A | * | 11/1993 | Schneider ............ B01D 63/021 156/169 |
| 6,004,511 A | | 12/1999 | Biscegli |
| 6,273,355 B1 | * | 8/2001 | Van Driel ............ B01D 63/02 156/172 |
| 2002/0039543 A1 | | 4/2002 | Ikeda et al. |

FOREIGN PATENT DOCUMENTS

| | | |
|---|---|---|
| JP | S52-41498 A | 3/1977 |
| JP | 5-36088 B2 | 5/1993 |
| JP | 5-214608 A | 8/1993 |
| JP | 4041254 B2 | 1/2008 |

OTHER PUBLICATIONS

International Search Report (PCT/ISA/210) mailed on Jun. 11, 2013, by the Japanese Patent Office as the International Searching Authority for International Application No. PCT/JP2013/057291.

Japanese Official Action ("Decision of Refusal") dated Mar. 28, 2017 in counterpart Japanese Application No. 2014-507678 (6 pages with English machine translation).

European Official Action dated Oct. 11, 2017 in corresponding European Patent Application 13770190.0 (9 pages).

Flavia Cassiola et al: "Polypropylene Hollow Fiber Oxygenators: Effect of the Sorption of Perfluoropolyethers", Artificial Organs, vol. 24, No. 3, Mar. 1, 2000 (Mar. 1, 2000), pp. 138-173.

* cited by examiner

PRODUCTION METHOD FOR MEDICAL INSTRUMENT AND MEDICAL INSTRUMENT

CROSS-REFERENCES TO RELATED APPLICATIONS

This application is a continuation of International Application No. PCT/JP2013/057291 filed on Mar. 14, 2013, and claims priority to Japanese Application No. 2012-070139 filed on Mar. 26, 2012, the entire content of both of which is incorporated herein by reference.

TECHNICAL FIELD

The present invention relates to a production method for a medical instrument and a medical instrument.

BACKGROUND DISCUSSION

In the related art, an oxygenator which performs gas exchange using a hollow fiber membrane layer constituted with a plurality of hollow fiber membranes is known (for example, see Japanese Patent No. 4041254).

The oxygenator described in Japanese Patent No. 4041254 has a housing, hollow fiber membrane layers which are housed in the housing and form a cylindrical shape as a whole, a blood inlet, a blood outlet, a gas inlet, and a gas outlet. In the oxygenator, through each hollow fiber membrane, gas exchange between blood and gas, that is, a process of adding oxygen and removing carbon dioxide occurs.

In the hollow fiber membrane layers having a shape of a cylindrical body, a plurality of hollow fiber membranes are integrated and laminated on one another. In each of the layers, hollow fiber membranes are wound one by one around the central axis of the cylindrical body, and in this state, the hollow fiber membranes travel between a partition at one end of the cylindrical body and a partition at the other end of the cylindrical body.

In an outward path heading toward the partition at the other end from the partition at one end, each hollow fiber membrane is wound at least once around the central axis of the cylindrical body. Moreover, in a homeward path heading toward the partition at one end from the partition at the other end, each hollow fiber membrane is also wound at least once around the central axis of the cylindrical body.

Each of the hollow fiber membranes wound as above has a problem in that the larger the number of times the membrane is wound, the greater the total length of the hollow fiber membranes become, and a degree of pressure loss of the gas passing through the inside of the hollow fiber membrane increases in proportion to the total length.

In this case, gas exchange performed through each hollow fiber membrane may not easily occur.

SUMMARY

The present application provides a production method for a medical instrument that makes it possible to inhibit pressure loss from occurring when fluid passes through the inside of a hollow fiber membrane and provides a medical instrument produced by the production method.

A production method for a medical instrument includes a hollow fiber membrane layer obtained from a base material having a plurality of hollow fiber membranes and forming a shape of a cylindrical body as a whole by integrating the plurality of hollow fiber membranes, the production method including producing the base material and obtaining the hollow fiber membrane layer by cutting each of both ends of the base material, each of the hollow fiber membranes is caused to sequentially pass through a first point which is set at one site of one end of the cylindrical body, a second point which is set at one site deviating from the first point by 20° to 175° around the central axis of the cylindrical body, a third point which is set at one site at the other end of the cylindrical body such that the third point is located in a position almost opposite to the first point across the central axis, a fourth point which is set at one site of the other end of the cylindrical body such that the fourth point is located in a position almost opposite to the second point across the central axis, and a fifth point which is set at one site that is in a position almost the same as the first point or set at one site that is closer to the one end than the first point, in an outward path heading toward the third point from the second point, the hollow fiber membrane reaches the third point from the second point at the shortest distance while being wound along the circumferential direction of the cylindrical body, in a homeward path heading toward the fifth point from the fourth point, the hollow fiber membrane reaches the fifth point from the fourth point at the shortest distance while being wound along the circumferential direction of the cylindrical body in the same direction as in the case of the outward path, and after a first line connecting the first point to the second point and a second line connecting the third point to the fourth point are imaginarily set respectively, a portion, which is closer to the other end than the first line, of one end of the base material is cut, and a portion, which is closer to one end than the second line, of the other end of the base material is cut.

The production method for a medical instrument can be configured so that when each of the hollow fiber membranes is caused to pass through the points from the first point to the second point, a restriction member for restricting the position of the hollow fiber membrane in the central axis direction is used.

In each of the hollow fiber membranes, a pathway sequentially passing through the points from the first point to the fifth point is repeated plural times.

According to one embodiment, the inner diameter of each of the hollow fiber membranes is preferably 50 μm to 700 μm.

According to another embodiment, the outer diameter of each of the hollow fiber membranes is preferably 100 μm to 900 μm.

The production method for a medical instrument can be configured such that, provided that the inner diameter of the hollow fiber membranes is $\varphi_1$ and the outer diameter of the hollow fiber membranes is $\varphi d_2$, a ratio $d_1/d_2$ between the inner diameter $\varphi_1$ and the outer diameter $\varphi_2$ is preferably 0.5 to 0.9.

According to another embodiment, the maximum outer diameter of the hollow fiber membrane layer is preferably 20 mm to 200 mm.

According to another embodiment, the length of the hollow fiber membrane layer extending along the central axis direction is preferably 30 mm to 250 mm.

A medical instrument comprises a core member possessing a central axis, a hollow fiber membrane layer obtained from a base material, the hollow fiber membrane being would alone a direction orthogonal to the central axis of the core member, wherein one winding of the hollow membrane begins at a first end of the core member, extends to an opposite end of the core member, and ends at the first end of the core member.

The medical instrument may be configured such that the hollow fiber membrane layer has either a function of performing gas exchange or a function of performing heat exchange.

The medical instrument is preferably an oxygenator.

Moreover, in the production method for a medical instrument, it is preferable for each of the hollow fiber membranes to be constituted with porous polypropylene.

Furthermore, in the production method for a medical instrument, it is preferable to use a cutter for cutting.

In the base material which will become the hollow fiber membrane layer, while each of the hollow fiber membranes is traveling back and forth along the central axis of the cylindrical body, that is, during a period of time when each of the hollow fiber membranes leaves the first point and then reaches the fifth point, each of the hollow fiber membranes is wound once around the central axis.

Consequentially, the length of each hollow fiber membrane from a partition to the other partition becomes shorter than the length of each hollow fiber membrane in the oxygenator described in, for example, Japanese Patent No. 4041254 (in the oxygenator, the hollow fiber membrane is wound once in each of the outward path and homeward path). As a result, it is possible to further inhibit pressure loss from occurring when fluid passes through the inside of the hollow fiber membrane, compared to the related art.

If the number of times the hollow fiber membrane is wound is reduced compared to that of the oxygenator of the related art, at a folding point of the hollow fiber membrane, the folding angle becomes an acute angle. Therefore, the hollow fiber membrane is not fixed to the point and easily deviates toward the other end.

In order to prevent such a problem, the folding angle of the hollow fiber membrane is made to be an obtuse angle by having a portion connecting the first point to the second point of the hollow fiber membrane and having a portion connecting the third point to the fourth point of the hollow fiber membrane, and as a result, the positional deviation can be prevented.

DETAILED DESCRIPTION

Figure 1:
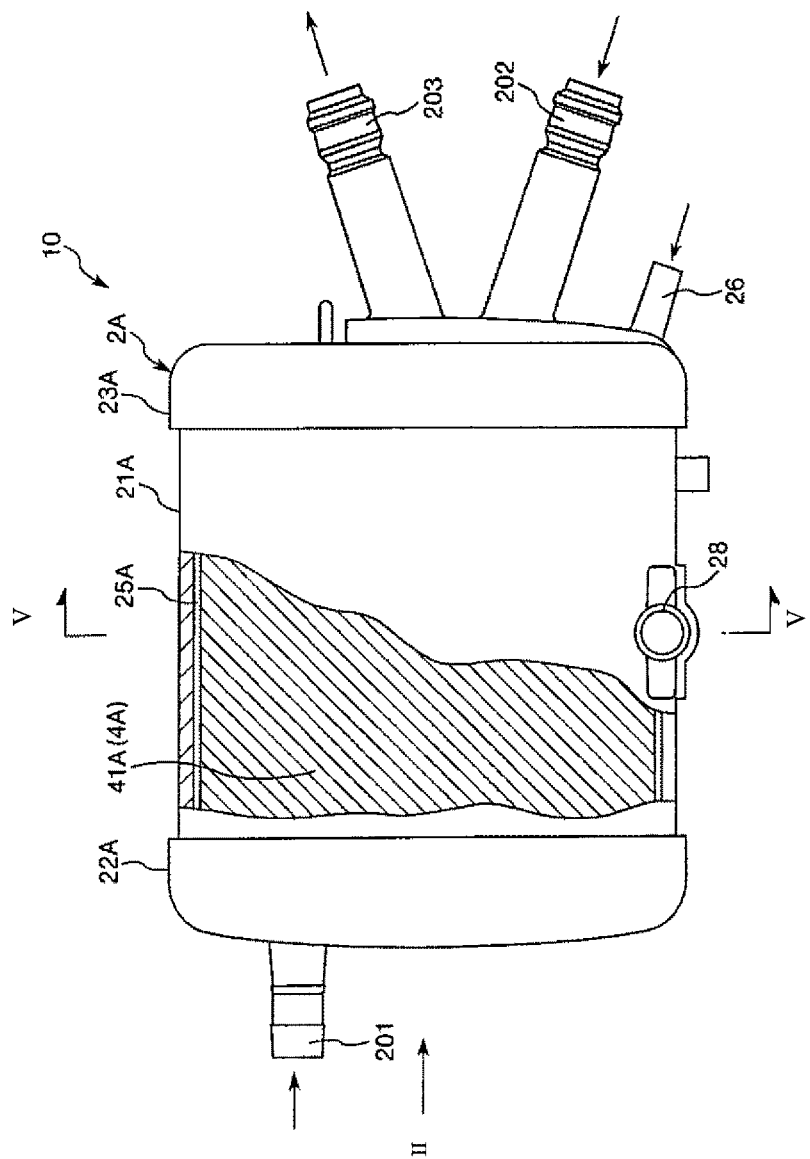
FIG. 1 is a plan view showing an embodiment in a case where a medical instrument produced by a production method for a medical instrument is applied to an oxygenator.

Hereinafter, a production method for a medical instrument and a medical instrument will be described in detail based on preferable embodiments shown in attached drawings.

Note that the left side in FIGS. 1, 3, 4, and 12 will be described as "left" or "left-hand side", and the right side in the drawings will be described as "right" or "right-hand side".

Furthermore, in FIG. 1 to FIG. 6, the inside of the oxygenator will be described as "blood inlet side" or "upstream side", and the outside of the oxygenator will be described as "blood outlet side" or "downstream side".

An oxygenator 10 shown in FIG. 1 to FIG. 5 has a cylindrically-shaped body.

The oxygenator 10 is an oxygenator equipped with a heat exchanger that includes a heat exchange portion 10B which is disposed in the inside of the oxygenator and performs heat exchange with blood and an oxygenator portion 10A which is disposed at the outer circumferential side of the heat exchange portion 10B and performs gas exchange with blood. The oxygenator 10 is installed in, for example, an extracorporeal blood circulation circuit.

The oxygenator 10 has a housing 2A, and the oxygenator portion 10A and the heat exchange portion 10B are housed in the housing 2A.

The housing 2A is constituted with a cylindrical housing main body 21A, a dish-shaped first cap 22A that seals a left-end opening of the cylindrical housing main body 21A, and a dish-shaped second cap 23A that seals a right-end opening of the cylindrical housing main body 21A.

The cylindrical housing main body 21A, the first cap 22A, and the second cap 23A are constituted with a resin material.

The first cap 22A and the second cap 23A are fixed to the cylindrical housing main body 21A, by a method such as fusion or bonding utilizing an adhesive.

In the outer circumferential portion of the cylindrical housing main body 21A, a tubular blood outlet port 28 is formed.

Figure 5:
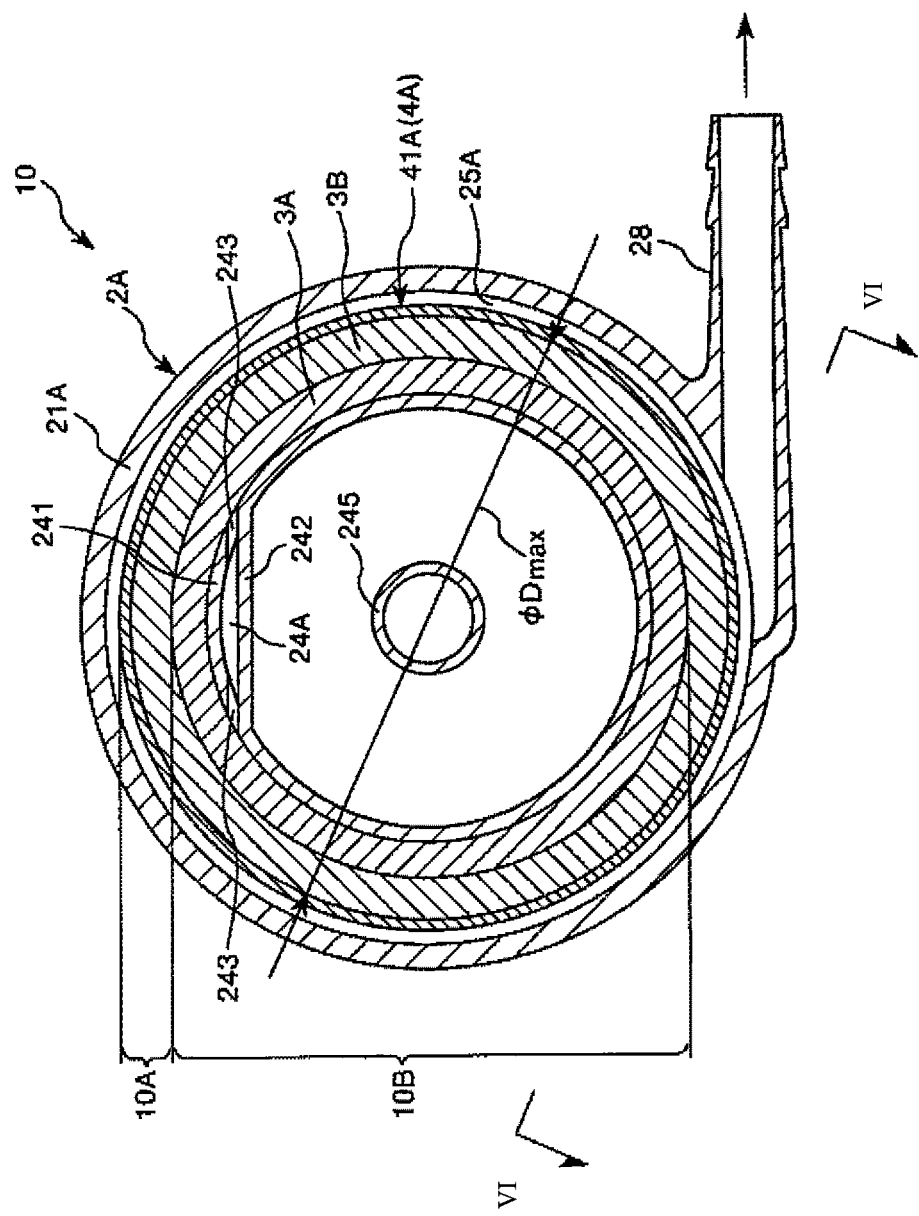
FIG. 5 is a cross-sectional view taken along the section line V-V in FIG. 1.

The blood outlet port 28 protrudes in a direction approximately corresponding to a tangential line of the outer circumferential surface of the cylindrical housing main body 21A (see FIG. 5).

In the first cap 22A, a tubular blood inlet port 201 and a gas outlet port 27 are formed in a state of protruding from the first cap 22A.

The blood inlet port 201 is formed in the end surface of the first cap 22A such that the central axis of the blood inlet port 201 becomes eccentric with respect to the center of the first cap 22A.

Figure 2:
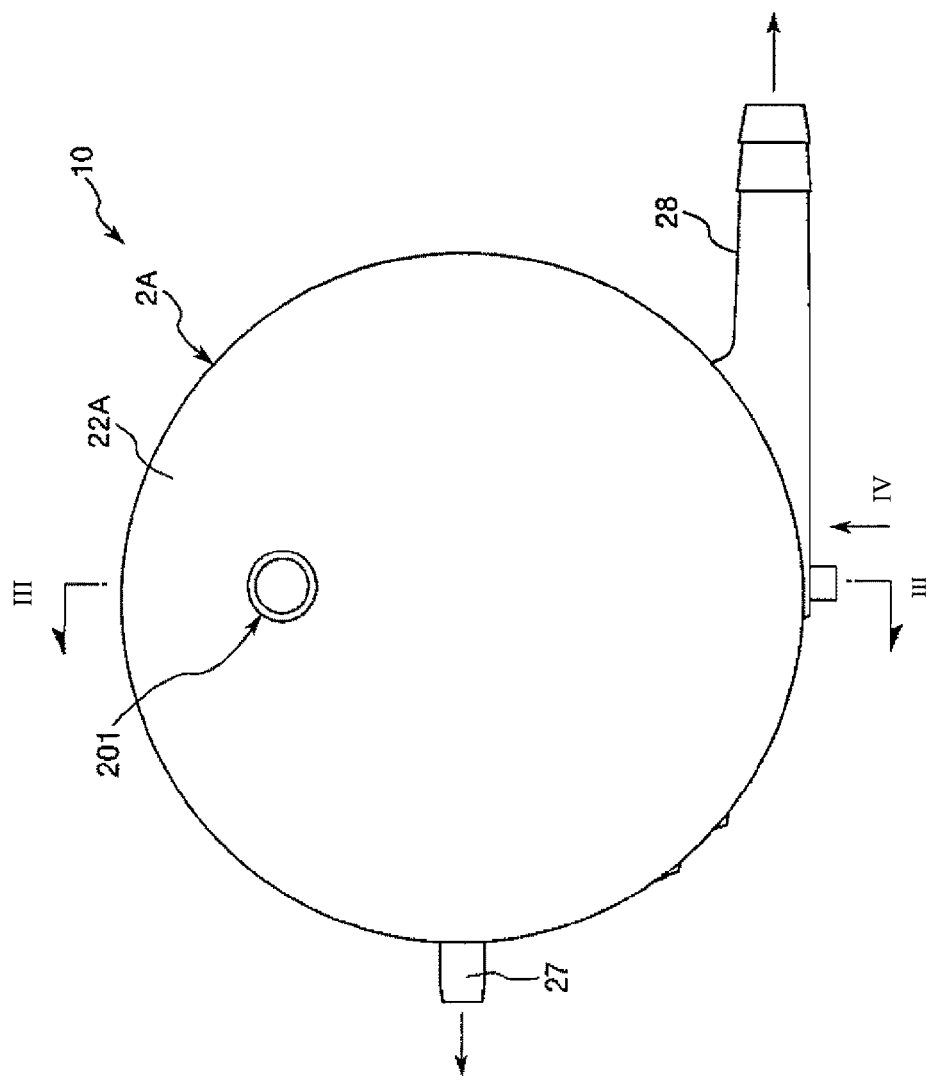
FIG. 2 is a view obtained when the oxygenator shown in FIG. 1 is viewed from the direction of arrow II.

The gas outlet port 27 is formed in the outer circumferential portion of the first cap 22A such that the central axis of the gas outlet port crosses the center of the first cap 22A (see FIG. 2).

In the second cap 23A, a tubular gas inlet port 26, a heat medium inlet port 202, and a heat medium outlet port 203 are formed in a state of protruding from the second cap 23A.

The gas inlet port 26 is formed at the edge of the end surface of the second cap 23A.

The heat medium inlet port 202 and the heat medium outlet port 203 are respectively formed in a portion approximately corresponding to the central portion of the end surface of the second cap 23A.

Moreover, each of the centerline of the heat medium inlet port 202 and the centerline of the heat medium outlet port 203 is slightly oblique to the centerline of the second cap 23A.

Note that the housing 2A does not need to form a shape of a complete cylinder as a whole. For example, the housing 2A may form a partially defective shape or form a shape to which a portion having a different shape has been added.

Figure 3:
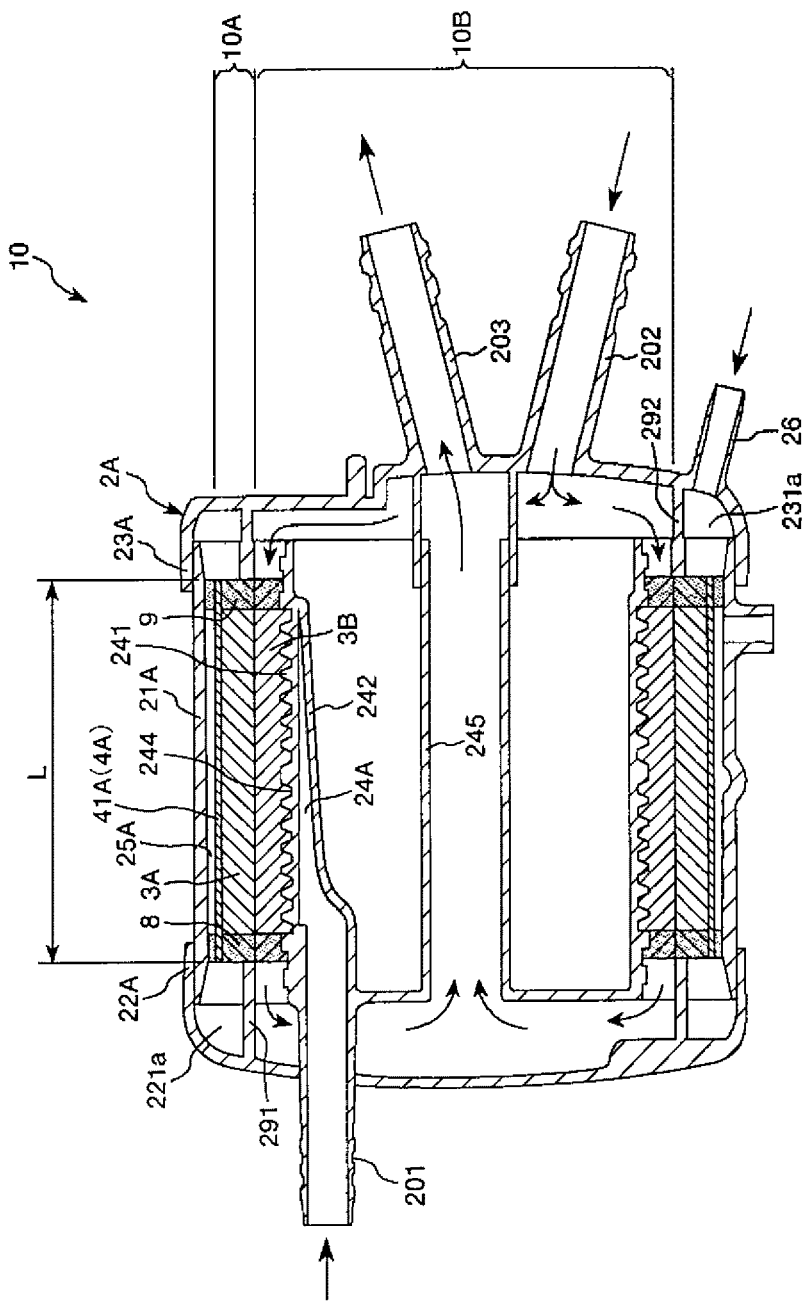
FIG. 3 is a cross-sectional view taken along the section line III-III in FIG. 2.
Figure 4:
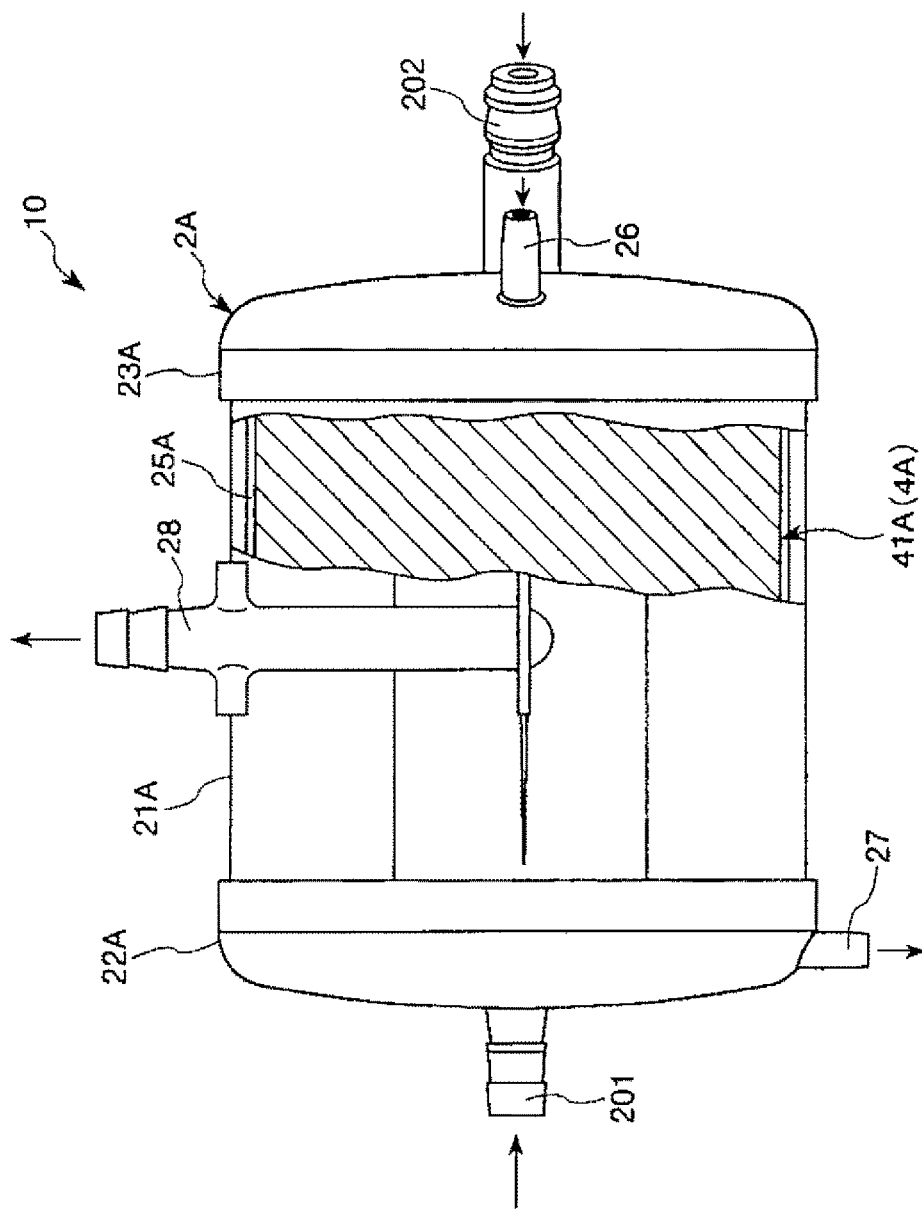
FIG. 4 is a view seen from the direction of arrow IV in FIG. 2.

As shown in FIG. 3 and FIG. 5, the oxygenator portion 10A, which forms a cylindrical shape along the inner circumferential surface of the housing 2A, is housed in the housing 2A.

The oxygenator portion 10A is constituted with a cylindrical hollow fiber membrane layer 3A and a filter member 41A as air bubble-removing means 4A disposed at the outer circumferential side (blood outlet portion side) of the hollow fiber membrane layer 3A.

The hollow fiber membrane layer 3A and the filter member 41A are disposed in order of the hollow fiber membrane layer 3A and the filter member 41A from a blood inlet side.

Figure 6:
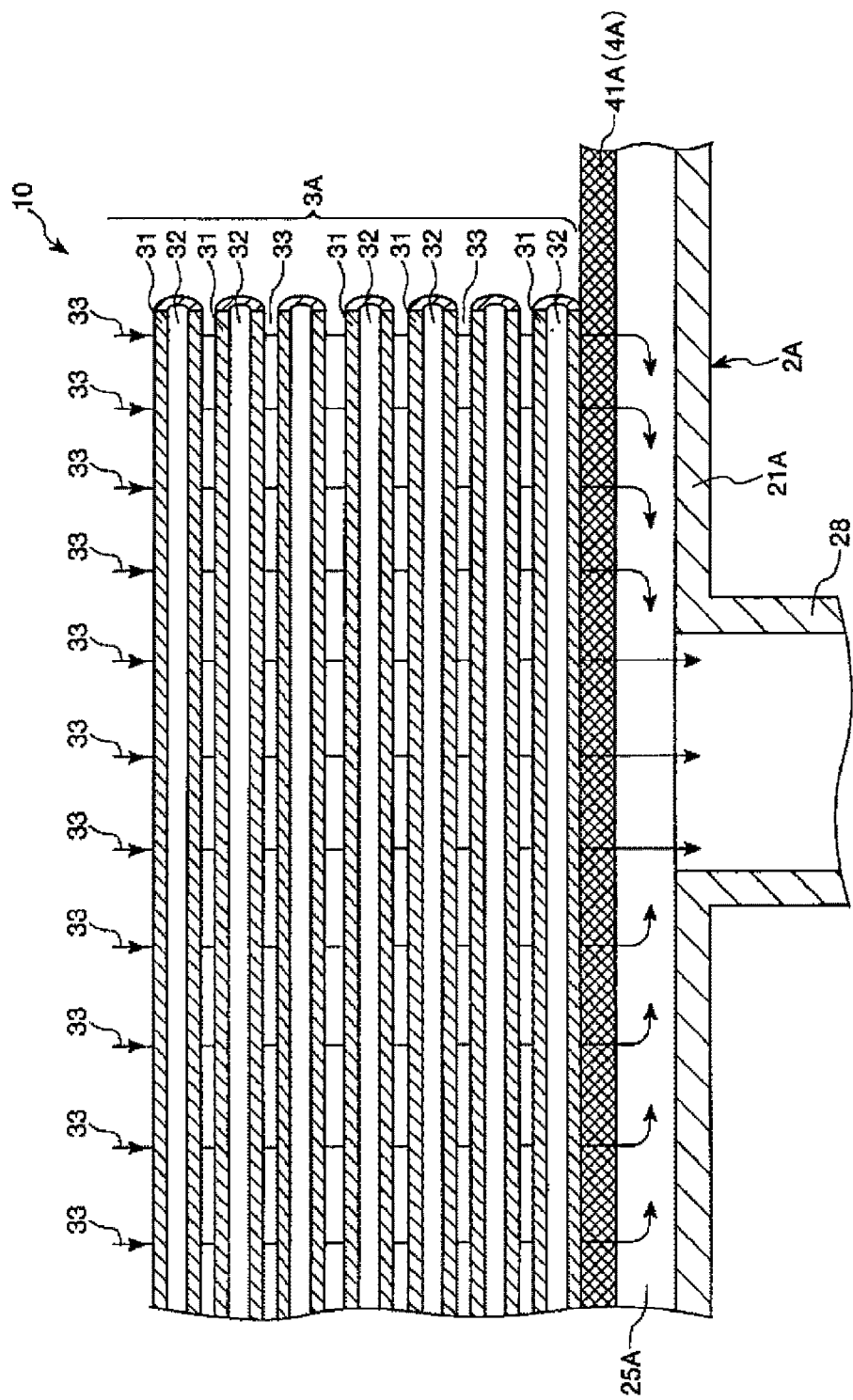
FIG. 6 is a cross-sectional view taken along the section line VI-VI in FIG. 5.

As shown in FIG. 6, the hollow fiber membrane layer 3A is constituted with a plurality of hollow fiber membranes 31 having a gas exchange function. In each hollow fiber membrane layer 3A, the hollow fiber membranes 31 are integrated.

As described later, the hollow fiber membrane layer 3A is obtained from a base material 3' which forms a shape of a cylindrical body as a whole.

A maximum outer diameter $\varphi D_{max}$ of the hollow fiber membrane layer 3A (base material 3') is preferably 20 mm to 200 mm and more preferably 40 mm to 150 mm (see FIG. 5).

Moreover, a length L of the hollow fiber membrane layer 3A extending along the central axis direction is preferably 30 mm to 250 mm and more preferably 50 mm to 200 mm (see FIG. 3).

If the hollow fiber membrane layer 3A satisfies the above conditions, a gas exchange function of the hollow fiber membrane layer 3A becomes excellent.

Figure 11:
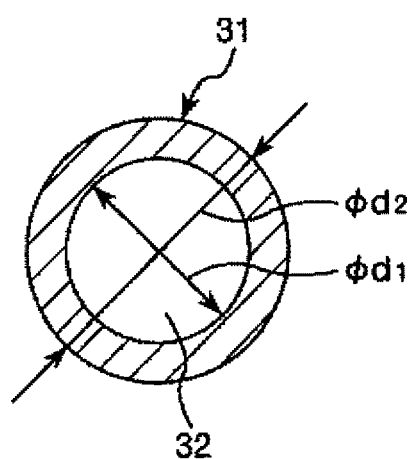
FIG. 11 is a lateral cross-sectional view of one hollow fiber membrane.

An inner diameter $\varphi d_1$ of each of the hollow fiber membranes 31 is preferably 50 μm to 700 μm, and more preferably 70 μm to 600 μm (see FIG. 11).

An outer diameter $\varphi d_2$ of each of the hollow fiber membranes 31 is preferably 100 μm to 900 μm, and more preferably 120 μm to 800 μm (see FIG. 11).

Moreover, a ratio $d_1/d_2$ between the inner diameter $\varphi_1$ and the outer diameter $\varphi_2$ is preferably 0.5 to 0.9, and more preferably 0.6 to 0.8.

In each of the hollow fiber membranes 31 satisfying such conditions, strength of the membranes can be maintained, and at the same time, a degree of pressure loss occurring when gas is caused to flow in the lumen (flow path 32) of the hollow fiber membrane 31 can be suppressed to a relatively low level.

For example, if the inner diameter $\varphi_1$ is larger than the aforementioned upper limit, the thickness of the hollow fiber membrane 31 is reduced, and depending on other conditions, the strength of the membrane is reduced.

Furthermore, if the inner diameter $\varphi_1$ is smaller than the aforementioned lower limit, depending on other conditions, a degree of pressure loss occurring when gas is caused to flow in the lumen of the hollow fiber membrane 31 becomes high.

In addition, a distance between the hollow fiber membranes 31 adjacent to each other is preferably 1/10 to 1/1 of the outer diameter $\varphi_2$.

A method for producing such a hollow fiber membrane 31 is not particularly limited. For example, by using a drawing process, a solid-liquid phase separation process, or the like and by appropriately regulating conditions such as a spinning speed and the amount of resin to be ejected, the hollow fiber membrane 31 having a prescribed inner diameter $\varphi d_1$ and outer diameter $\varphi d_2$ can be produced.

As materials constituting each hollow fiber membrane 31, for example, hydrophobic polymer materials such as polypropylene, polyethylene, polysulfone, polyacrylonitrile, polytetrafluoroethylene, and polymethylpentene are used. As the materials, polyolefin-based resins are preferable, and polypropylene is more preferable.

Moreover, it is more preferable for the hollow fiber membrane 31 to have micropores formed in the wall portion by a drawing process or a solid-liquid phase separation process. That is, it is more preferable for the hollow fiber membrane 31 to be constituted with porous polypropylene.

If the hollow fiber membrane 31 is formed of such a material, gas exchange between blood and the hollow fiber membrane 31 reliably occurs.

As shown in FIG. 3, both ends of each hollow fiber membrane 31, that is, a left end (one end) and a right end (the other end) of each hollow fiber membrane 31 are respectively fixed to the inner surface of the cylindrical housing main body 21A by partitions 8 and 9.

The partitions 8 and 9 are constituted with, for example, a potting material such as polyurethane or silicone rubber or an adhesive.

Moreover, a space between the cylindrical housing main body 21A and the heat exchange portion 10B is packed with the hollow fiber membrane layer 3A almost without a void. Accordingly, the hollow fiber membrane layer 3A forms an approximately cylindrical shape as a whole.

Consequentially, for the cylindrical housing main body 21A having the similar shape, a high packing efficiency resulting from the hollow fiber membranes 31 is obtained (a dead space is reduced), and this makes a contribution to miniaturization and improvement of performance of the oxygenator portion 10A.

At the outside of each hollow fiber membrane 31 between the partition 8 and the partition 9 inside the housing 2A, (that is, in a void between the hollow fiber membranes 31) a blood flow path 33 in which blood flows toward the lower side from the upper side in FIG. 6 is formed.

At the upstream side of the blood flow path 33, that is, at the upstream side from the heat exchange portion 10B positioned at the inner circumferential side of the oxygenator portion 10A, as a blood inlet portion for blood having flowed in from the blood inlet port 201, a blood inlet side space 24A that is in communication with the blood inlet port 201 is formed (see FIG. 3 and FIG. 5).

The blood inlet side space 24A is a space constituted with a first cylinder member 241 that forms a cylindrical shape and a plate piece 242 that is disposed inside the first cylinder member 241 while facing a portion of the inner circumferential portion of the first cylinder member 241.

The blood having flowed into the blood inlet side space 24A can flow down toward the entire blood flow path 33 through a plurality of side holes 243 formed in the first cylinder member 241.

At the downstream side of the blood flow path 33, a cylindrical void is formed between the outer circumferential surface of the filter member 41A and the inner circumferential surface of the cylindrical housing main body 21A. The void forms a blood outlet side space 25A.

The blood outlet side space 25A and the blood outlet port 28 which is in communication with the blood outlet side space 25A constitute a blood outlet portion.

The blood outlet portion has the blood outlet side space 25A. Accordingly, a space that allows the blood having passed through the filter member 41A to flow toward the blood outlet port 28 is secured, whereby the blood can be smoothly discharged.

Moreover, between the blood inlet side space 24A and the blood outlet side space 25A, the hollow fiber membrane layer 3A, the filter member 41A, and the blood flow path 33 are present.

Furthermore, at the downstream side (blood outlet portion side) of the hollow fiber membrane layer 3A, the air bubble-removing means 4A, which has a function of capturing air bubbles in the blood and removing the air bubbles from the blood, is disposed.

The air bubble-removing means 4A has the filter member 41A.

The filter member 41A has a function of capturing air bubbles present in the blood flowing in the blood flow path 33.

The filter member 41A is constituted with a sheet-like member (hereinafter, also simply referred to as "sheet") that forms an approximately rectangular shape. The filter member 41A is formed of the sheet wound up in the form of a cylinder.

Both ends of the filter member 41A are fixed by the partitions 8 and 9 respectively, and as a result, the filter member 41A is fixed to the housing 2A (see FIG. 3).

The filter member 41A is disposed such that the inner circumferential surface of the filter membrane 41A comes into contact with the surface of the downstream side (blood outlet portion side) of the hollow fiber membrane layer 3A. The filter member 41A approximately covers the entire surface of the downstream side of the hollow fiber membrane layer 3A.

Moreover, even when there are air bubbles in the blood flowing in the blood flow path 33, the filter member 41A can capture these air bubbles (see FIG. 6).

Furthermore, by the blood flow, the air bubbles captured by the filter member 41A are pushed into each hollow fiber membrane 31 in the vicinity of the filter member 41A. As a result, the air bubbles are removed from the blood flow path 33.

As shown in FIG. 3, at the inside of the first cap 22A, a rib 291 forming an annular shape is formed in a state of protruding from the inside of the first cap 22A.

Moreover, a first chamber 221a is constituted with the first cap 22A, the rib 291, and the partition 8.

The first chamber 221a is a gas outlet chamber from which gas flows out.

The left-end opening of each of the hollow fiber membranes 31 is opened to and is in communication with the first chamber 221a.

Meanwhile, at the inside of the second cap 23A, a rib 292 forming an annular shape is formed in a state of protruding from the inside of the second cap 23A.

Moreover, a second chamber 231a is constituted with the second cap 23A, the rib 292, and the partition 9.

The second chamber 231a is a gas inlet chamber into which gas flows.

The right-end opening of each of the hollow fiber membranes 31 is opened to and is in communication with the second chamber 231a.

The lumen of each hollow fiber membrane 31 constitutes the flow path 32 (gas flow path) in which gas flows.

The gas inlet port 26 and the second chamber 231a constitute the gas inlet portion positioned at the upstream side of the flow path 32. Moreover, the gas outlet port 27 and the first chamber 221a constitute the gas outlet portion positioned at the downstream side of the flow path 32.

The heat exchange portion 10B is disposed inside the oxygenator portion 10A.

The heat exchange portion 10B has a hollow fiber membrane layer 3B.

The hollow fiber membrane layer 3B is the same as the hollow fiber membrane layer 3A, except that the hollow fiber membrane layer 3B performs heat exchange.

That is, similarly to the hollow fiber membrane layer 3A in the oxygenator portion 10A, the hollow fiber membrane layer 3B performing heat exchange is constituted with the plurality of hollow fiber membranes 31. In the hollow fiber membrane layer 3B, the hollow fiber membranes 31 are integrated, and a void between the hollow fiber membranes 31 becomes the blood flow path 33.

Furthermore, the hollow fiber membrane layer 3B is also obtained from the base material 3' forming a shape of a cylindrical body as a whole.

Herein, regarding the hollow fiber membrane layer 3B, differences between the hollow fiber membrane layer 3B and the aforementioned hollow fiber membrane layer 3A will be mainly described.

As shown in FIG. 3, in the hollow fiber membrane layer 3B, each of the two ends of the hollow fiber membrane layer 3B (that is, each of the left end (one end) and right end (the other end) of the hollow fiber membrane layer 3B) is fixed to the inner surface of the cylindrical housing main body 21A by the partitions 8 and 9.

Moreover, the inner circumferential portion of the hollow fiber membrane layer 3B is engaged with a concave-convex portion 244 formed in the outer circumferential portion of the first cylinder member 241.

By being engaged in this manner and being fixed by the partitions 8 and 9, the hollow fiber membrane layer 3B is reliably fixed to the cylindrical housing main body 21A. As a result, it is possible to reliably prevent an occurrence of positional deviation of the hollow fiber membrane layer 3B when the oxygenator 10 is being used.

At the inside of the first cylinder member 241, a second cylinder member 245 is disposed in a state of being concentric with the first cylinder member 241.

Moreover, as shown in FIG. 3, a heat medium (for example, water) having flowed from the heat medium inlet port 202 sequentially passes through the flow path 32 (heat medium flow path) of each hollow fiber membrane 31 of the hollow fiber membrane layer 3B positioned at the outer circumferential side of the first cylinder member 241 and the inside of the second cylinder member 245, and is then discharged out of the heat medium outlet port 203.

Furthermore, when the heat medium passes through the flow path 32 of each hollow fiber membrane 31, heat exchange (heating or cooling) is performed between the blood, which comes into contact with the hollow fiber membrane 31, and the heat medium.

If the heat exchange portion 10B is disposed inside the oxygenator portion 10A as described above, the following effects are exerted.

That is, first, the oxygenator portion 10A and the heat exchange portion 10B can be efficiently housed in a single housing 2A, and an area of dead space is reduced. Accordingly, gas exchange can be efficiently performed in the small oxygenator 10.

Second, the oxygenator portion 10A and the heat exchange portion 10B are in a state of being close to each other. Accordingly, it is possible to allow the blood having undergone heat exchange in the heat exchange portion 10B to rapidly flow into the oxygenator portion 10A while preventing the blood from releasing or absorbing heat as far as possible.

As materials constituting the hollow fiber membranes 31 that constitute the heat exchange portion 10B, it is possible to use, for example, polyethylene terephthalate, polycarbonate, polyurethane, nylon, polystyrene, and vinyl chloride, in addition to those exemplified as the materials constituting the hollow fiber membranes 31 that constitute the oxygenator portion 10A.

Next, blood flow in the oxygenator 10 of the present embodiment will be described.

In the oxygenator 10, the blood having flowed from the blood inlet port 201 sequentially passes through the blood inlet side space 24A and the side holes 243, and flows into the heat exchange portion 10B.

In the heat exchange portion 10B, the blood keeps flowing in the blood flow path 33 toward the downstream side, and in this state, the blood undergoes heat exchange (heating or cooling) by coming into contact with the surface of each of the hollow fiber membranes 31.

The blood having undergone heat exchange in this manner flows into the oxygenator portion 10A.

Thereafter, in the oxygenator portion 10A, the blood flows in the blood flow path 33 toward the downstream side.

Meanwhile, the gas (oxygen-containing gas) having been supplied from the gas inlet port 26 is distributed to each flow path 32 of each of the hollow fiber membranes 31 from the second chamber 231a. After flowing in the flow path 32, the gas is integrated in the first chamber 221a and discharged out of the gas outlet port 27.

The blood flowing in the blood flow path 33 comes into contact with the surface of each of the hollow fiber membranes 31, whereby gas exchange (addition of oxygen or removal of carbon dioxide) is performed between the blood and the gas flowing in the flow path 32.

When there are air bubbles in the blood having undergone gas exchange, these air bubbles are captured by the filter member 41A, and as a result, the air bubbles are prevented from flowing out toward the downstream side of the filter member 41A.

The blood, which has undergone gas exchange and removal of air bubbles as described above, flows out of the blood outlet port 28.

The oxygenator 10 as a medical instrument including the hollow fiber membrane layers 3A and 3B is produced by the production method for a medical instrument.

The production method includes producing a base material 3' of the hollow fiber membrane layer 3A (also performed for the hollow fiber membrane layer 3B), obtaining the hollow fiber membrane layer 3A by cutting each of both ends of the base material 3', and assembling the hollow fiber membrane layer 3A and the like by housing them in the housing 2A.

Figure 7:
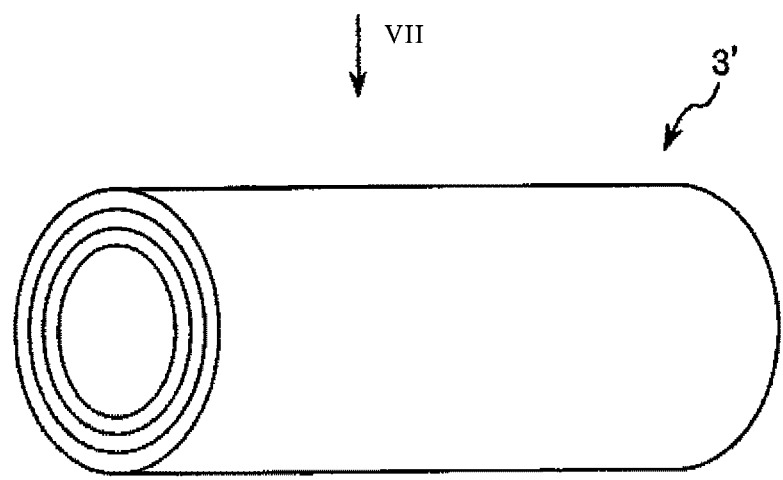
FIG. 7 is a perspective view showing a base material which will become a hollow fiber membrane layer included in the oxygenator shown in FIG. 1.

As shown in FIG. 7, the base material 3' is obtained by laminating the plurality of hollow fiber membranes 31 in the form of layers. The number of layers laminated on one another is not particularly limited, but is preferably, for example, 3 to 40.

Figure 8:
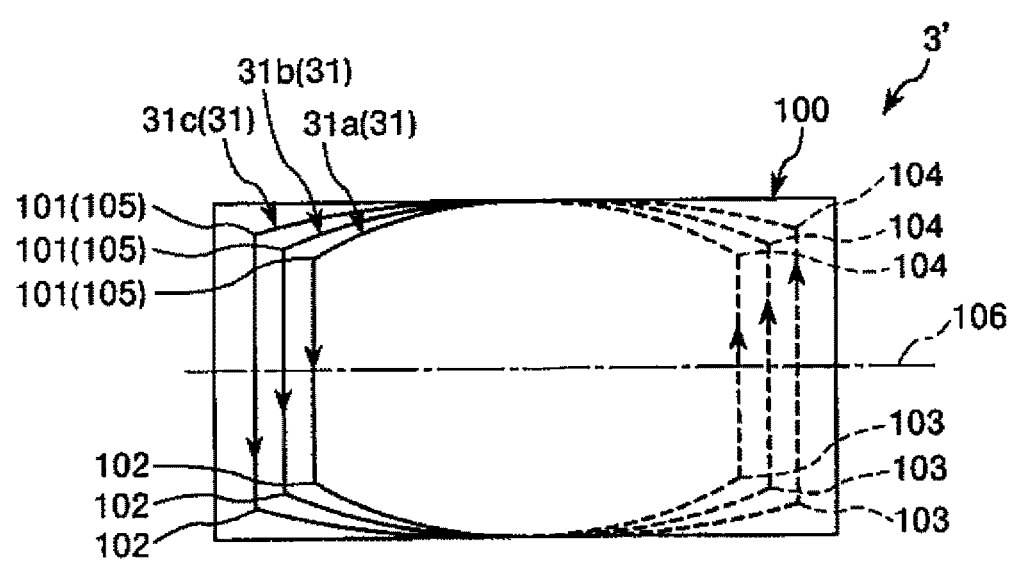
FIG. 8 is a view seen from the direction of arrow VIII in FIG. 7.

Moreover, in FIG. 8, three (hollow fiber membranes 31a, 31b, and 31c) out of the plurality of hollow fiber membranes 31 in the innermost layer positioned at the innermost side are representatively described.

Figure 9:
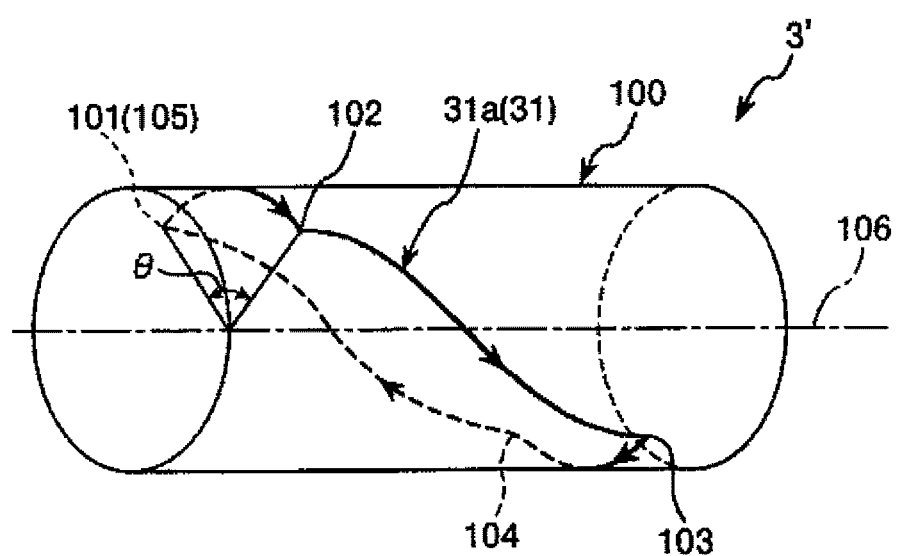
FIG. 9 is a perspective view showing one hollow fiber membrane layer in the base material shown in FIG. 7.
Figure 10:
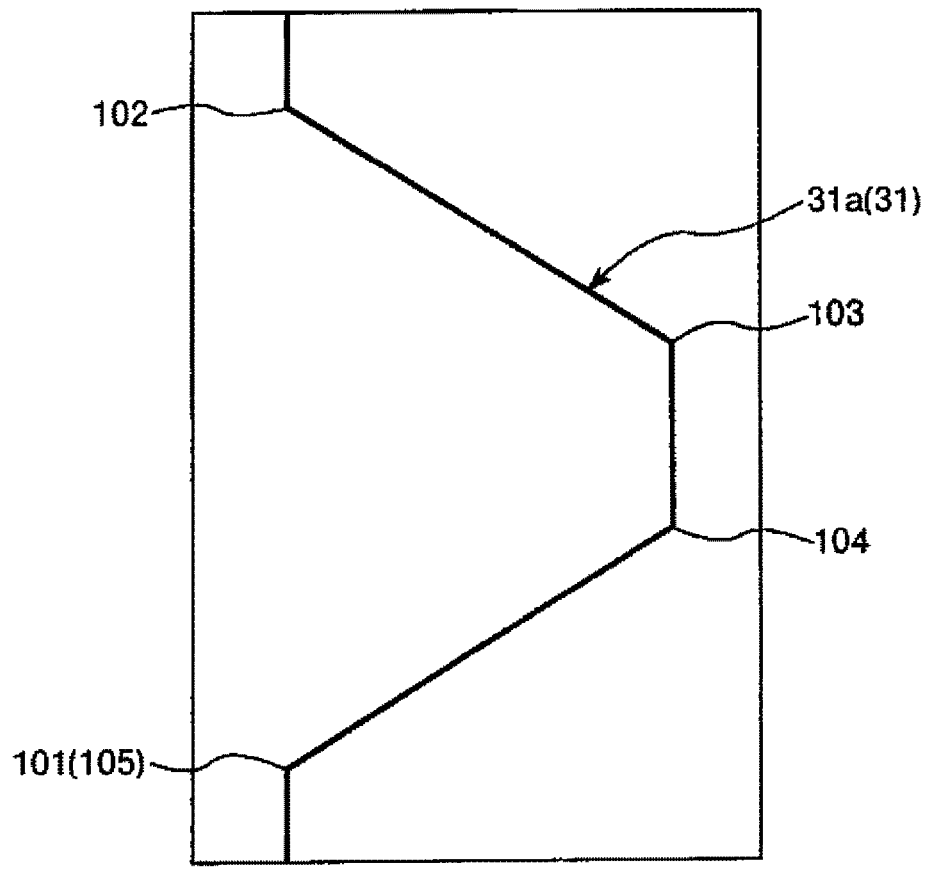
FIG. 10 is a development view of one hollow fiber membrane layer shown in FIG. 9.

Furthermore, in each of FIG. 9 and FIG. 10, among the hollow fiber membranes 31a to 31c, the hollow fiber membrane 31a is representatively described.

Figure 12:
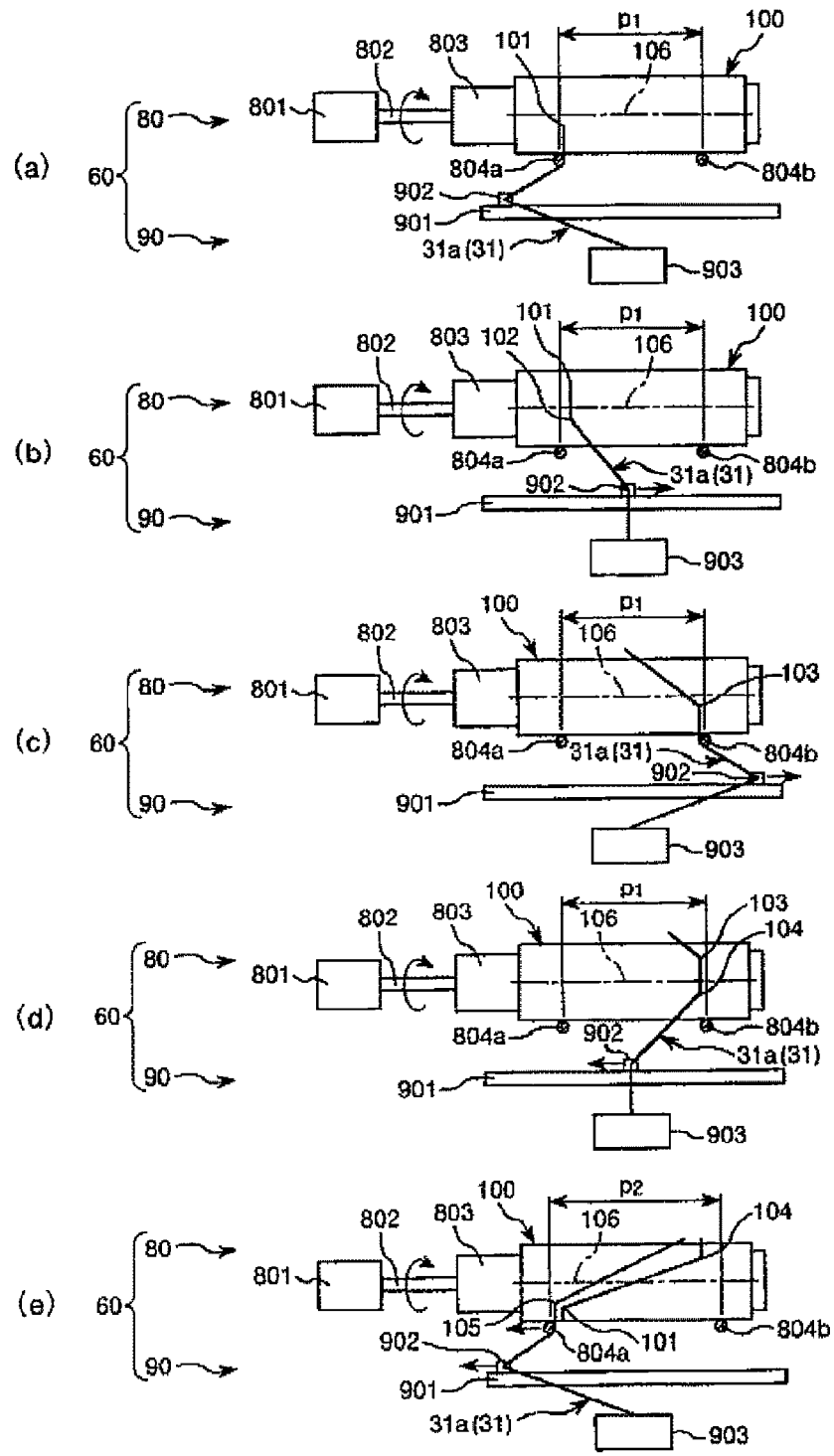
FIGS. 12(a)-12(e) are views sequentially showing steps of producing the base material shown in FIG. 7.

In addition, as a winding apparatus 60 that winds the plurality of hollow fiber membranes 31 and laminates them in the form of layers, an apparatus including a rotary device 80 and a winder device 90 is used (see FIG. 12).

The rotary device 80 includes a motor 801, a motor shaft 802 which is connected to the motor 801 and rotates by the operation of the motor 801, and a support member 803 which is fixed to the left end of the motor shaft 802 and on which a cylindrical core member 100 around which the hollow fiber membrane 31 is wound is detachably mounted.

Moreover, the rotary device 80 has rod-like restriction members 804a and 804b that temporarily restrict the position of the hollow fiber membrane 31 which is supplied from the winder device 90 and wound around the core member 100.

The restriction member 804 is in a position in which the restriction member 804 is at a right angle to a central axis 106 of the core member 100 mounted on the support member 803.

In addition, the restriction members 804a and 804b are supported such that they can approach each other and can be separated from each other along the direction of the central axis 106 of the core member 100.

The winder device 90 has a main body portion 901, a guiding portion 902 which is supported to be able to reciprocate in the main body portion 901 in the left-and-right direction (horizontal direction) and guides the hollow fiber membrane 31, and a bobbin (supply portion) 903 which supplies the hollow fiber membrane 31 to the core member 100.

In the winding apparatus 60 constituted as above, while the core member 100 is being rotated by the rotary device 80, the hollow fiber membranes 31 are supplied one by one from the winder device 90 to the core member 100 (alternatively, the plurality of hollow fiber membranes 31 is simultaneously supplied to the core member 100).

At this time, if the reciprocation of the guiding portion 902 and the position of the restriction members 804a and 804b in the axial direction of the core member 100, that is, a distance between the restriction members 804a and 804b separated from each other are appropriately controlled, the hollow fiber membrane 31 is wound in a direction oblique to the central axis of the core member 100. That is, the hollow fiber membrane 31 is helically wound or wound along a direction orthogonal to the central axis of the core member 100 (see FIG. 12).

Note that, in the winding apparatus 60, a first cylinder member 241 may be used instead of the core member 100.

Figure 13:
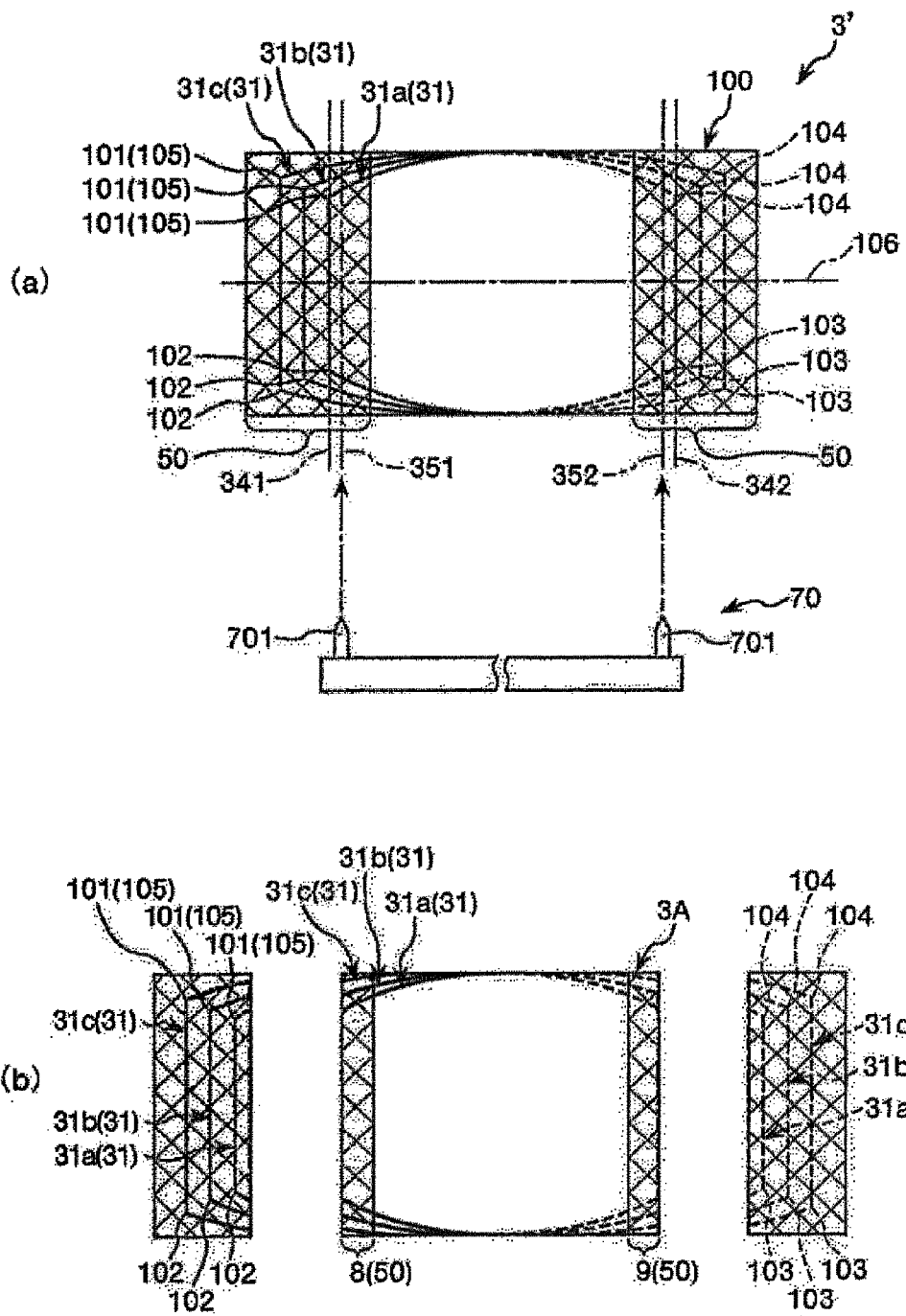
FIGS. 13(a) and 13(b) are views sequentially showing steps of cutting the base material shown in FIG. 7.

As a cutting apparatus 70 that cuts the base material 3', an apparatus having a cutter (cutting tool) 701 is used (see part (a) of FIG. 13).

The cutting apparatus 70 is stationary, and the base material 3' is cut by being brought to the cutter 701.

Note that, the cutting apparatus 70 is not limited to an apparatus constituted with the cutter 701. For example, the apparatus may be constituted to shoot water jets or constituted to emit laser beams.

As described above, similarly to the base material 3', the core member 100, around which each of the hollow fiber membranes 31 constituting the base material 3' is wound, forms a cylindrical shape.

Moreover, five points are set on the outer circumference of the core member 100, and each of the hollow fiber membranes 31 is caused to sequentially pass through the five points (see FIG. 8, FIG. 9, FIG. 10, and FIG. 12).

A first point 101 is set at one site of a left end (one end) of the core member 100.

A second point 102 is set at one site which deviates from the first point 101 by an angle θ around a central axis 106 of the core member 100.

The angle θ is not particularly limited, and is preferably 20° to 175° and more preferably 30° to 150°.

A third point 103 is set at one site of a right end (the other end) of the core member 100 such that the third point 103 is located in a position almost opposite to the first point 101 across the central axis 106.

Accordingly, provided that the central portion of the central axis 106 in the longitudinal direction is taken as a center of symmetry, a positional relationship (point symmetry) in which the first point 101 and the third point 103 become almost symmetrical to each other around the center is established between these points.

A fourth point 104 is set at one site of the right end of the core member 100 such that the fourth point 104 is located in a position almost opposite to the second point 102 across the central axis 106.

That is, provided that the central portion of the central axis 106 in the longitudinal direction is taken as a center of symmetry, a positional relationship (point symmetry) in which the second point 102 and the fourth point 104 become almost symmetrical to each other around the center is established between these points.

A fifth point 105 is set at a site located in a position almost the same as the first point 101.

Note that, the fifth point 105 may be set at one site which is closer to the left end than the first point 101 is, on the outer circumference of the core member 100.

Herein, "almost" means that the fifth point 105 is not overlapped with the first point 101 and is in a position adjacent to the first point 101 as shown in, for example, part (e) of FIG. 12.

Furthermore, by using the winding apparatus 60 including the rotary device 80 and the winder device 90, the hollow fiber membrane 31 is wound around the core member 100 on which the first point 101 to the fifth point 105 have been set.

As shown in part (a) of FIG. 12, in the rotary device 80, the restriction member 804a and the restriction member 804b are separated from each other at a pitch $p_1$.

Moreover, the restriction member 804a is attached to the core member 100, in a position almost the same as the first point 101 in the direction of the central axis 106.

In addition, the guiding portion 902 of the winder device 90 is positioned at the leftmost side in part (a) of FIG. 12.

This position is closer to the left side than the restriction member 804a is, in the direction of the central axis 106.

Moreover, one end of the hollow fiber membrane 31a that has been pulled out of the winder device 90 is fixed to the first point 101 and is engaged with the restriction member 804a.

When the motor 801 of the rotary device 80 is operated after the state shown in part (a) of FIG. 12 is established, by the restriction member 804a, the position of the hollow fiber membrane 31a in the direction of the central axis 106 is restricted. Consequentially, from the first point 101 to the second point 102, the hollow fiber membrane 31a is reliably wound.

Thereafter, the guiding portion 902 of the winder device 90 moves to the right side as shown in part (b) of FIG. 12.

Note that, the operation of the motor 801 is continued until the hollow fiber membrane 31a reaches the fifth point 105 from the first point 101.

When the guiding portion 902 of the winder device 90 further moves to the rightmost side as shown in part (c) of FIG. 12 after the state shown in part (b) of FIG. 12 is established, the hollow fiber membrane 31a is engaged with the restriction member 804b.

Note that, in the meantime, the hollow fiber membrane 31a reaches the third point 103 from the second point 102 at the shortest distance while being helically wound along the circumferential direction of the core member 100.

Furthermore, as shown in part (c) of FIG. 12, by the restriction member 804b, the position of the hollow fiber membrane 31a in the direction of the central axis 106 is restricted.

As a result, from the third point 103 to the fourth point 104, the hollow fiber membrane 31a is reliably wound (see part (d) of FIG. 12).

Subsequently, when the guiding portion 902 of the winder device 90 returns to the leftmost side in part (e) of FIG. 12, the hollow fiber membrane 31a is engaged again with the restriction member 804a.

Note that, in the meantime, the hollow fiber membrane 31a reaches the fifth point 105 from the fourth point 104 at the shortest distance while being helically wound along the circumferential direction of the core member 100.

In addition, at this time, the restriction member 804a and the restriction member 804b are separated from each other at a pitch $p_2$ (>pitch $p_1$).

For example, oxygenators of the related art include an oxygenator which has hollow fiber membrane layers consisting of a plurality of hollow fiber membranes laminated on one another and forming a shape of a cylindrical body as a whole. In each of the layers, the hollow fiber membranes travel between one end and the other end of the cylindrical body while being helically wound one by one around the central axis of the cylindrical body.

In such an oxygenator of the related art, the first point and the second point are located in the same position, and the third point and the fourth point are also located in the same position.

Moreover, in this oxygenator, each of the hollow fiber membranes is wound at least once around the central axis of the cylindrical body, in an outward path heading toward the other end from one end of the cylindrical body. In a homeward path heading toward one end from the other end, each of the hollow fiber membranes is also wound at least once around the central axis of the cylindrical body.

In each of the hollow fiber membranes wound as above, the larger the number of times each hollow fiber membrane is wound is, the greater the total length of the hollow fiber membranes become, and a degree of pressure loss of the gas passing through the inside of the hollow fiber membrane increases in proportion to the total length.

However, in the base material 3' to be the hollow fiber membrane layer 3A, while the hollow fiber membrane 31 wound up is moving back and forth around the core member 100, that is, during a period of time when the hollow fiber membrane leaves the first point 101 and then reaches the fifth point 105, the hollow fiber membrane 31 is wound only once around the central axis 106 (see FIG. 9).

Figure 14:
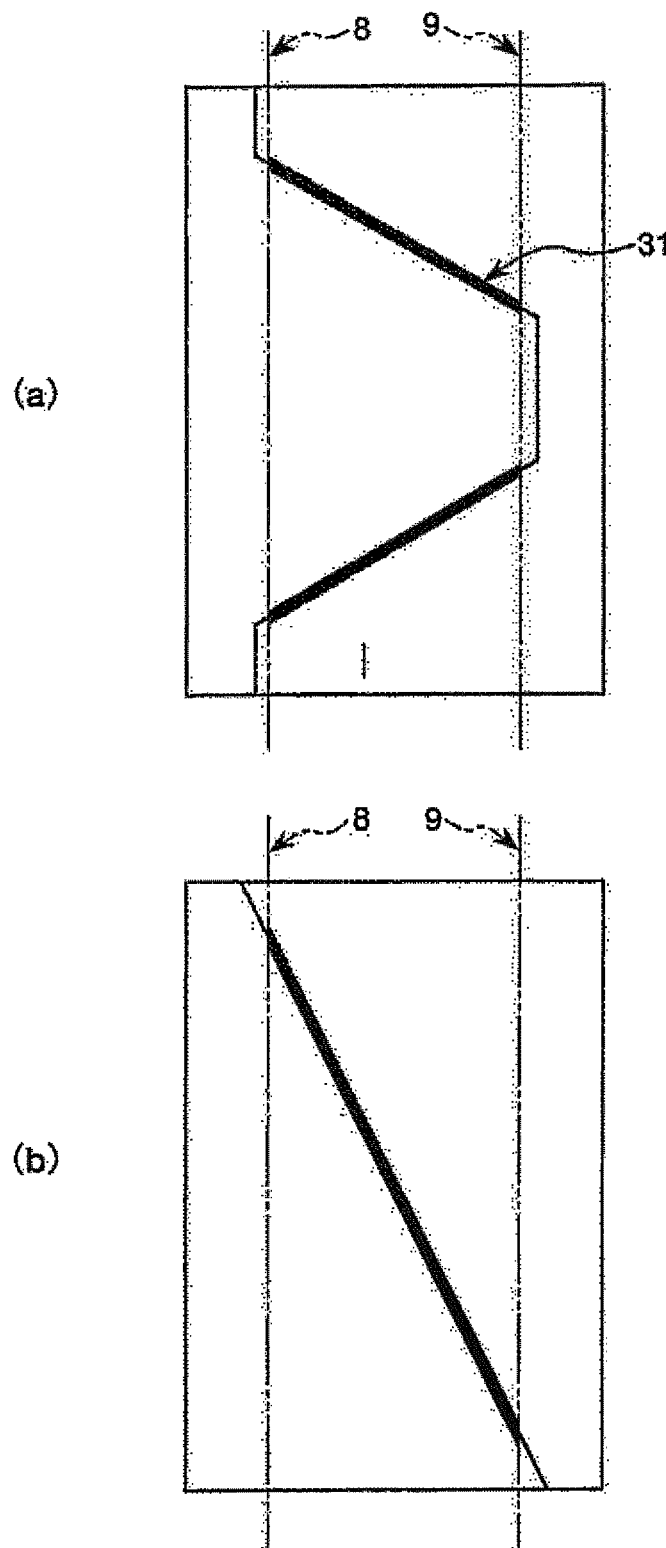
FIGS. 14(a) and 14(b) are views comparing the length of one hollow fiber membrane in the oxygenator shown in FIG. 1 with the length of one hollow fiber membrane in an oxygenator of the related art (FIG. 14(a) shows the length of the former, and FIG. 14(b) shows the length of the latter).

Consequentially, as shown in FIG. 14, the length of each hollow fiber membrane 31 from the partition 8 to the other partition 9 (see part (a) of FIG. 14) becomes shorter than the length of one hollow fiber membrane in the oxygenator of the related art (see part (b) of FIG. 14). As a result, it is possible to further inhibit pressure loss from occurring when gas passes through the inside of the hollow fiber membrane 31, compared to the related art.

If the number of times the hollow fiber membrane 31 is wound is reduced compared to that of the oxygenator of the related art, at a folding point of the hollow fiber membrane 31, the folding angle becomes an acute angle. Therefore, the hollow fiber membrane 31 is not fixed to the point and easily deviates toward the other end.

In order to prevent this problem, the folding angle of the hollow fiber membrane 31 becomes an obtuse angle by a portion connecting the first point 101 to the second point 102 of the hollow fiber membrane 31 and a portion connecting the third point 103 to the fourth point 104 of the hollow fiber membrane 31, and as a result, the positional deviation can be prevented.

Moreover, in the winding apparatus 60, after winding of the hollow fiber membrane 31a is completed, hollow fiber membranes 31b and 31c can be wound similarly to the hollow fiber membrane 31a.

In this case, each of the first point 101 (fifth point 105) and the second point 102 that the hollow fiber membrane 31b passes through is positioned at the left side from the first point 101 (fifth point 105) and the second point 102 that the hollow fiber membrane 31a passes through. Moreover, each of the third point 103 and the fourth point 104 that the hollow fiber membrane 31b passes through is positioned at the right side from the third point 103 and the fourth point 104 that the hollow fiber membrane 31a passes through (see FIG. 8).

In addition, each of the first point 101 (fifth point 105) and the second point 102 that the hollow fiber membrane 31c passes through is positioned at the left side from the first point 101 (fifth point 105) and the second point 102 that the hollow fiber membrane 31b passes through. Furthermore, each of the third point 103 and the fourth point 104 that the hollow fiber membrane 31c passes through is positioned at the right side from the third point 103 and the fourth point 104 that the hollow fiber membrane 31b passes through (see FIG. 8).

Moreover, in the winding apparatus 60, a layer, which is formed of the hollow fiber membranes 31 as above, can be used as an innermost layer, and another layer which is formed of the hollow fiber membranes 31 can be laminated on the innermost layer.

By the step performed as above, the base material 3' is obtained.

Note that it is preferable for both ends of the base material 3' to be fixed to each hollow fiber membrane 31 by a potting material 50.

The potting material 50 becomes the partitions 8 and 9.

In order to fix the base material 3' as above, first, the base material 3' having not been fixed by the potting material is housed in a housing.

Next, liquid polyurethane as a material constituting the potting material is injected into the housing.

Thereafter, each housing is treated with a centrifuge, and then the liquid polyurethane is dried.

In this manner, both ends of the base material 3' are in a state of being fixed by the potting material.

Thereafter, the base material 3' is taken out of the housing.

Each of the two ends of the potting material 50—containing base material 3' obtained is cut, thereby obtaining the hollow fiber membrane layer 3A.

As shown in part (a) of FIG. 13, a first line (first imaginary line) 341 connecting the first point 101 to the second point 102 of the hollow fiber membrane 31 (hollow fiber membrane 31a in the constitution shown in part (a) of FIG. 13), which is positioned at the innermost side among a plurality of hollow fiber membranes 31 in the base material 3' in a plan view, and a second line (second imaginary line) 342 connecting the third point 103 to the fourth point 104 of the same hollow fiber membrane 31 are imaginarily set respectively.

Thereafter, a portion, which is closer to the right end than the first line 341 at the left end of the base material 3', is taken as a first cutting line 351, and a portion, which is closer to the left end than the second line 342 at the right end of the base material 3', is taken as a second cutting line 352.

Note that it is preferable for the first cutting line 351 to be set in a position separated from the first line 341 by 0.5 mm to 20 mm.

Moreover, it is preferable for the second cutting line 352 to be set in a position separated from the second line 342 by 0.5 mm to 20 mm.

Furthermore, by using the cutting apparatus 70, each of the first cutting line 351 and the second cutting line 352 is cut.

In this manner, as shown in part (b) of FIG. 13, the base material 3' is divided into three members, and the member positioned at the center becomes the hollow fiber membrane layer 3A.

Note that the members at both ends are discarded respectively.

The hollow fiber membrane layer 3A is thus obtained.

Next, the hollow fiber membrane layer 3A, the hollow fiber membrane layer 3B which is obtained from the base material 3' similarly to the hollow fiber membrane layer 3A, and additionally, the housing 2A, the filter member 41A, and the like constituting the oxygenator 10 are prepared.

Thereafter, these members are sequentially assembled, thereby obtaining the oxygenator 10.

Note that, in order to fix the filter member 41A to the hollow fiber membrane layer 3B, first, the filter member 41A is wound around the hollow fiber membrane layer 3B. Thereafter, by using a method almost the same as the fixing method using the potting material 50, the filter member 41A is fixed.

As described above, in the oxygenator 10, it is possible to inhibit pressure loss from occurring when gas passes through the inside of the hollow fiber membranes 31 of the hollow fiber membrane layer 3A.

As a result, gas exchange can be easily and reliably performed through each of the hollow fiber membranes 31.

Furthermore, in the hollow fiber membrane layer 3A, it is also possible to inhibit or prevent so-called blood shunting.

In addition, it is possible to inhibit pressure loss from occurring even when a heat medium passes through the inside of the hollow fiber membranes 31 of the hollow fiber membrane layer 3B.

As a result, heat exchange can be easily and reliably performed through each of the hollow fiber membranes 31.

Up to now, the production method for a medical instrument and the medical instrument have been described in regard to the embodiments shown in the drawings, but the present application is not limited to these configurations. Each portion constituting the medical instrument can be replaced with a portion having any constitution that can perform the same function.

Moreover, any constituent may be added to the medical instrument.

Moreover, in the aforementioned embodiments, each of the hollow fiber membranes constituting each of the hollow fiber membrane layers of the oxygenator portion is the same as each of the hollow fiber membranes constituting each of the hollow fiber membrane layers of the heat exchange portion. However, the present application is not limited to these configurations, and for example, one (the former) hollow fiber membrane may be finer than the other (the latter) hollow fiber membrane, or alternatively, both the hollow fiber membranes may be constituted with different materials.

Furthermore, inside the heat exchange portion, a hollow fiber membrane layer having the same function as each of the hollow fiber membrane layers of the oxygenator portion, that is, a hollow fiber membrane layer (second hollow fiber membrane layer) having a gas exchange function may be disposed.

In addition, in the aforementioned embodiments, the heat exchange portion includes hollow fiber membrane layers having a heat exchange function. However, the present application is not limited in this manner, and the heat exchange portion may include a so-called bellows-type heat exchanger.

The exchanger can be constituted with metal materials such as stainless steel and aluminum or resin materials such as polyethylene and polycarbonate.

Moreover, in the production method for a medical instrument, a pathway in which each hollow fiber membrane sequentially passes through the points from the first point to the fifth point may be repeated plural times.

If such a pathway is repeated plural times, each hollow fiber membrane can be continuously wound, and consequentially, production efficiency of the base material is increased.

The production method for a medical instrument is a method for producing a medical instrument which includes a hollow fiber membrane layer obtained from a base material having a plurality of hollow fiber membranes and forming a shape of a cylindrical body as a whole by integrating the plurality of hollow fiber membranes. The production method includes producing the base material and obtaining the hollow fiber membrane layer by cutting each of both ends of the base material, in which each of the hollow fiber membranes is caused to sequentially pass through a first point which is set at one site of one end of the cylindrical body, a second point which is set at one site deviating from the first point by 20° to 175° around the central axis of the cylindrical body, a third point which is set at one site at the other end of the cylindrical body such that the third point is located in a position almost opposite to the first point across the central axis, a fourth point which is set at one site of the other end of the cylindrical body such that the fourth point is located in a position almost opposite to the second point across the central axis, and a fifth point which is set at one site that is in a position almost the same as the first point or set at one site that is closer to the one end than the first point, in an outward path heading toward the third point from the second point, the hollow fiber membrane reaches the third point from the second point at the shortest distance while being wound along the circumferential direction of the cylindrical body, in a homeward path heading toward the fifth point from the fourth point, the hollow fiber membrane reaches the fifth point from the fourth point at the shortest distance while being wound along the circumferential direction of the cylindrical body in the same direction as in the case of the outward path, and after a first line connecting the first point to the second point and a second line connecting the third point to the fourth point are imaginarily set respectively, a portion, which is closer to the other end than the first line, of one end of the base material is cut, and a portion, which is closer to one end than the second line, of the other end of the base material is cut.

Therefore, it is possible to inhibit pressure loss from occurring when fluid passes through the inside of the hollow fiber membrane.

The detailed description above describes embodiments of method of production for a medical instrument and a medical instrument representing examples of the medical instrument and the method of the present invention. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A production method for a medical instrument which includes a hollow fiber membrane layer obtained from a base material, the base material having a plurality of hollow fiber membranes formed in a cylindrical shaped body by integrating the plurality of hollow fiber membranes, the cylindrical shaped body having a central axis, the production method comprising:

producing the base material;

obtaining the hollow fiber membrane layer by cutting each of both ends of the base material, wherein each of the hollow fiber membranes is sequentially passed through a first point which is set at a first site proximal one end of the cylindrical shaped body, a second point which is set at a second site deviating from the first point by 20° to 175° around the central axis of the cylindrical shaped body, the second point of each said hollow fiber membrane being disposed at substantially the same axial position as the first point, such that the portion of said hollow fiber membrane disposed between the first point and the second point extends in the circumferential direction along the shortest path, a third point which is set at a third site at the other end of the cylindrical shaped body such that the third point is located in a position almost opposite to the first point across the central axis, a fourth point which is set at a fourth site of the other end of the cylindrical body such that the fourth point is located in a position almost opposite to the second point across the central axis, and a fifth point which is set at a fifth site that is in a position almost the same as the first point or set at a site that is closer to the one end than the first point, each of the hollow fiber membranes being wound only once around the central axis of the cylindrical shaped body in a pathway sequentially passing through the points from the first point to the fifth point;

in an outward path heading toward the third point from the second point, the hollow fiber membrane reaches the third point from the second point at the shortest distance while being wound along a circumferential direction of the cylindrical shaped body, in a homeward path heading toward the fifth point from the fourth point, the hollow fiber membrane reaches the fifth point from the fourth point at the shortest distance while being wound along the circumferential direction of the cylindrical shaped body in the same direction as in the case of the outward path, and after a first line connecting the first point to the second point and a second line connecting the third point to the fourth point are set respectively, a portion, which is closer to the other end than the first line, of one end of the base material is cut, and a portion, which is closer to one end than the second line, of the other end of the base material is cut.

2. The production method for a medical instrument according to claim 1,
wherein when each of the hollow fiber membranes passes through the points from the first point to the second point, a restriction member for restricting the position of the hollow fiber membrane in the central axis direction is used.

3. The production method for a medical instrument according to claim 1,
wherein in each of the hollow fiber membranes, the pathway sequentially passing through the points from the first point to the fifth point is repeated plural times.

4. The production method for a medical instrument according to claim 1,
wherein an inner diameter of each of the hollow fiber membranes is 50 μm to 700 μm.

5. The production method for a medical instrument according to claim 1,
wherein an outer diameter of each of the hollow fiber membranes is 100 μm to 900 μm.

6. The production method for a medical instrument according to claim 1, wherein when an inner diameter of each of the hollow fiber membranes is $\varphi d_1$ and an outer diameter of each of the hollow fiber membranes is $\varphi d_2$, a ratio $d_1/d_2$ between the inner diameter $\varphi d_1$ and the outer diameter $\varphi d_2$ is 0.5 to 0.9.

7. The production method for a medical instrument according to claim 1,
wherein a maximum outer diameter of the hollow fiber membrane layer is 20 mm to 200 mm.

8. The production method for a medical instrument according to claim 1,
wherein a length of the hollow fiber membrane layer extending along the central axis direction is 30 mm to 250 mm.

9. A medical instrument produced by the production method for a medical instrument according to claim 1.

10. The medical instrument according to claim 9,
wherein the hollow fiber membrane layer performs at least one of gas exchange and heat exchange.

11. The medical instrument according to claim 10, wherein the medical instrument is an oxygenator.

12. A medical instrument comprising:
a core member possessing a central axis;
a plurality of integrated hollow fiber membranes forming a hollow fiber membrane layer;
each of the hollow fiber membranes extending helically in a direction orthogonal to the central axis of the core member;

wherein each of the hollow fiber membranes begins at a first end of the core member, extends to an opposite end of the core member, and ends at the first end of the core member while winding only once around the central axis of the core member;

wherein one winding of the hollow fiber membrane passes through a first point which is set at a first site of the first end of the core member, a second point which is set at a second site deviating from the first point by 20° to 175° around the central axis of the core member, the second point of each said hollow fiber membrane being disposed at substantially the same axial position as the first point, such that the portion of said hollow fiber membrane disposed between the first point and the second point extends in the circumferential direction along the shortest path, a third point which is set at a third site at the opposite end of the core member such that the third point is located in a position almost opposite to the first point across the central axis, a fourth point which is set at a fourth site of the opposite end of the cylindrical body such that the fourth point is located in a position almost opposite to the second point across the central axis, and a fifth point which is set at a fifth site that is in a position almost the same as the first point or set at a site that is closer to the first end than the first point, in an outward path heading toward the third point from the second point; and wherein the hollow fiber membrane reaches the third point from the second point at the shortest distance while being wound along a circumferential direction of the core member, in a homeward path heading toward the fifth point from the fourth point, the hollow fiber membrane reaches the fifth point from the fourth point at the shortest distance while being wound along the circumferential direction of the core member in the same direction as in the case of the outward path.

13. The medical instrument according to claim 12,
wherein in each of the hollow fiber membranes, a pathway sequentially passing through the points from the first point to the fifth point is repeated plural times.

14. The medical instrument according to claim 12,
wherein an inner diameter of the hollow fiber membrane is 50 μm to 700 μm.

15. The medical instrument according to claim 12,
wherein an outer diameter of the hollow fiber membrane is 100 μm to 900 μm.

16. The medical instrument according to claim 12,
wherein when an inner diameter of the hollow fiber membrane is $\varphi d_1$ and an outer diameter of the hollow fiber membrane is $\varphi d_2$, a ratio $d_1/d_2$ between the inner diameter $\varphi d_1$ and the outer diameter $\varphi d_2$ is 0.5 to 0.9.

17. The medical instrument according to claim 12,
wherein a maximum outer diameter of the hollow fiber membrane layer is 20 mm to 200 mm.

18. The medical instrument according to claim 12,
wherein a length of the hollow fiber membrane layer extending along the central axis direction is 30 mm to 250 mm.

19. The medical instrument according to claim 12,
wherein the hollow fiber membrane layer performs at least one of gas exchange and heat exchange.

* * * * *